(12) United States Patent
Abdul-Khalek

(10) Patent No.: US 9,869,220 B2
(45) Date of Patent: Jan. 16, 2018

(54) APPARATUS AND METHOD FOR REMOVAL OF GAS PHASE ARTIFACTS FROM ENGINE EXHAUST DURING TESTING

(71) Applicant: Southwest Research Institute, San Antonio, TX (US)

(72) Inventor: Imad Said Abdul-Khalek, San Antonio, TX (US)

(73) Assignee: SOUTHWEST RESEARCH INSTITUTE, San Antonio, TX (US)

( * ) Notice: Subject to any disclaimer, the term of this patent is extended or adjusted under 35 U.S.C. 154(b) by 65 days.

(21) Appl. No.: 14/254,674

(22) Filed: Apr. 16, 2014

(65) Prior Publication Data

US 2015/0300225 A1    Oct. 22, 2015

(51) Int. Cl.
*B01D 50/00* (2006.01)
*B01D 39/14* (2006.01)
*B01D 39/20* (2006.01)
*B01D 39/06* (2006.01)
*F01N 3/02* (2006.01)
(Continued)

(52) U.S. Cl.
CPC ............... *F01N 3/02* (2013.01); *B01D 53/02* (2013.01); *G01N 15/065* (2013.01); *G01N 33/0014* (2013.01); *B01D 2253/108* (2013.01); *B01D 2257/30* (2013.01); *B01D 2257/702* (2013.01); *G01N 1/2205* (2013.01); *G01N 15/0618* (2013.01); *G01N 2015/0046* (2013.01)

(58) Field of Classification Search
CPC ....... F01N 3/02; B01D 53/02; B01D 2257/30; B01D 2257/04; B02D 2253/108; G01N 2001/2223; G01N 1/2208; G01N 1/24; G01N 14/0255; G01N 1/2202
See application file for complete search history.

(56) References Cited

U.S. PATENT DOCUMENTS 5,302,191 A * 4/1994 Koutrakis ............ B01D 50/002
                                                        55/485
5,763,360 A * 6/1998 Gundel .................... B01J 20/26
                                                        422/70
(Continued)

FOREIGN PATENT DOCUMENTS

JP      2002295244 A    10/2002
WO    2003086568 A1    10/2003
(Continued)

OTHER PUBLICATIONS

Khalek, "2007 Diesel Particulate Measurement Research," Coordinating Research Council Project E-66 Phase 1, http://www.crcao.org/reports/recentstudies2005/Final%20Rport-10415-Project%20E-66-Phase%201--R3.pdf.
(Continued)

*Primary Examiner* — Amber R Orlando
(74) *Attorney, Agent, or Firm* — Grossman, Tucker et al.

(57) ABSTRACT

An apparatus and method for removal of gas phase artifacts from engine exhaust undergoing evaluation for the presence of particulate matter as collected on a particulate matter filter. More specifically, the disclosure relates to an apparatus and method for removal of gas phase artifacts from engine exhaust being tested and prior to the exhaust reaching a particulate matter (PM) filter. Such removal provides that the PM filter indicates relatively more accurate evaluation of the particulate matter present.

14 Claims, 3 Drawing Sheets

(51) Int. Cl.
*B01D 53/02* (2006.01)
*G01N 15/06* (2006.01)
*G01N 33/00* (2006.01)
*G01N 1/22* (2006.01)
*G01N 15/00* (2006.01)

(56) References Cited

U.S. PATENT DOCUMENTS

| | | |
|---|---|---|
| 6,864,198 B2 | 3/2005 | Merkel |
| 7,537,629 B2* | 5/2009 | Shih .................... G01N 15/0255 55/462 |
| 8,528,320 B2 | 9/2013 | Nagaoka et al. |
| 2003/0108465 A1 | 6/2003 | Voss et al. |
| 2003/0192830 A1 | 10/2003 | Memmott et al. |
| 2005/0126395 A1* | 6/2005 | Blackburn ......... B01J 20/28095 96/108 |
| 2005/0169826 A1* | 8/2005 | Li ....................... B01D 53/9431 423/244.06 |
| 2006/0172428 A1* | 8/2006 | McDermott ......... G01N 1/2205 436/63 |
| 2007/0055438 A1* | 3/2007 | Twigg ...................... F01N 3/035 701/109 |
| 2008/0134894 A1* | 6/2008 | Tsai ....................... G01N 30/08 96/5 |
| 2010/0184587 A1* | 7/2010 | Hao .................... B01D 53/9436 502/66 |
| 2012/0090411 A1* | 4/2012 | Perlinger ............. G01N 1/2205 73/863.12 |
| 2013/0192463 A1* | 8/2013 | Wu ....................... G01N 1/2205 95/82 |
| 2014/0004013 A1 | 1/2014 | Park et al. |
| 2014/0219878 A1* | 8/2014 | Mccool .................. B01J 29/068 422/168 |
| 2014/0301926 A1* | 10/2014 | Hatfield ............... B01D 53/944 423/213.5 |

FOREIGN PATENT DOCUMENTS

| | | | |
|---|---|---|---|
| WO | WO2012054382 | * | 4/2012 |
| WO | WO2013044115 | * | 3/2013 |

OTHER PUBLICATIONS

Khalek, "The Particulars of Diesel Particle Emissions," http://www.swri.org/3pubs/ttoday/Spring06/PDFs/Particulars.pdf.
Khalek, "2007 Diesel Particulate Measurement Research," Coordinating Research Council Project E-66 Phase 3, http://www.crcao.org/reports/recentstudies2007/E-66-3/E-66%20Phase%203%20Final%Report%R8-%20IAK-Revised%2010SEP2007.pdf.
http://www.sunlab.com/products-services/denuders.html.

* cited by examiner

APPARATUS AND METHOD FOR REMOVAL OF GAS PHASE ARTIFACTS FROM ENGINE EXHAUST DURING TESTING

STATEMENT OF GOVERNMENT SPONSOR

This invention was made with government support under contract no. GS-07F-6087P awarded by the United States Environmental Protection Agency. The government has certain rights in the invention.

FIELD OF THE INVENTION

The present disclosure is directed at an apparatus and method for removal of gas phase artifacts from engine exhaust during testing. More specifically, the disclosure relates to an apparatus and method for removal of gas phase artifacts from engine exhaust during testing and prior to the exhaust reaching a particulate matter (PM) filter. Such removal provides that the PM filter indicates relatively more accurate filter performance for evaluation of engine exhaust for regulatory compliance.

BACKGROUND

Particulate matter (PM) emitted from engines and vehicles is defined by the United States Environmental Protection Agency as the materials collected from a dilute engine exhaust on a high efficiency (>99% particle removal) filter that is maintained at 47° C.±5° C. In addition, such filter medium is typically a polytetrafluroethylene (PTFE) membrane or PTFE coated glass fiber filter. With the increased stringency in emissions regulations, the PM filter weight gain during a typical heavy-duty or light-duty highway engine laboratory test dropped from a few milligrams for late 1980s engines to a few micrograms for 2007 engines and beyond.

With the reduction in PM emissions and PM collection on a filter during an engine and/or a vehicle test, filter sampling, handling and weighing has become important to the accuracy and reduced variability in filter measurement. One source that leads to measurement uncertainty is gas phase artifacts collection by the PM filter during sampling. Ideally, the filter should only collect airborne particles that amount to liquid droplets and/or solid particles and/or particles with adsorbed layers of particle phase hydrocarbons or sulfate species. However, in practice, during filter collection, the PM filter tends to adsorb materials from the gas phase (gas phase artifacts) significantly increasing the uncertainty in filter measurements. Some main sources of these gas phase artifacts are gas phase hydrocarbons and sulfuric acid that are present in engine exhaust.

Accordingly, when evaluating a selected engine exhaust for regulatory compliance, it is important to ensure that the determination of particulate matter presence is as accurate as possible and not adversely influenced by artifacts that compromise the ability to correctly determine particulate levels. Such need is even more pressing in the face of the relatively more stringent particulate matter levels for engine exhaust noted above.

SUMMARY

A method for removal of gas phase artifacts from an exhaust stream of a hydrocarbon combustion engine undergoing evaluation for the presence of particulate matter as collected on a particulate matter filter. The method includes positioning a gas phase denuder in the exhaust stream undergoing evaluation for particulate matter at a location upstream of the particulate matter filter, wherein the exhaust includes solid particles or liquid droplets in the size range of 5 nm to 1000 nm, and wherein the gas phase denuder comprises a cellular substrate having an aluminum-zeolite coating. This is followed by feeding the exhaust stream through the gas phase denuder and removing 90% by weight or volume of the gas phase artifacts in the exhaust stream wherein the gas phase artifacts comprise one or more of:
  (a) hydrocarbons having four or more carbon atoms; or
  (b) sulfur dioxide and sulfate species of the formulas $SO_2$, $SO_3$, $SO_4^{2-}$, $H_2SO_4$ and $(NH_4)_2SO_4$.
The gas phase denuder then provides penetration of 95% to 100% of the solid particles or liquid droplets in the exhaust which then pass through the denuder for collection on the particulate filter.

The present disclosure in apparatus form relates to a filtration apparatus for hydrocarbon combustion engine exhaust containing gas phase artifacts and solid or liquid droplets, the exhaust stream undergoing evaluation for the presence of particulate matter as collected on a particulate matter filter. The apparatus comprises a particulate matter filter for collecting the solid or liquid droplets and a gas phase denuder in the exhaust stream at a location upstream of the particulate filter, wherein the exhaust includes solid particles or liquid droplets in the size range of 5 nm to 1000 nm, and wherein the gas phase denuder comprises a cellular substrate having an aluminum-zeolite coating that absorbs 90% by weight or volume of one or more of:
  (a) hydrocarbons having four or more carbon atoms; or
  (b) sulfur dioxide and sulfate species of the formulas $SO_2$, $SO_3$, $SO_4^{2-}$, $H_2SO_4$ and $(NH_4)_2SO_4$;
The gas phase denuder then provides for 95% to 100% penetration of the solid particles or liquid droplets for collection on the particulate matter filter.

BRIEF DESCRIPTION OF THE DRAWINGS

The above-mentioned and other features of this disclosure, and the manner of attaining them, may become more apparent and better understood by reference to the following description of embodiments described herein taken in conjunction with the accompanying drawings, wherein.

DETAILED DESCRIPTION

As noted above, the present disclosure is directed at an apparatus and method to avoid gas phase adsorption on a PM filter during exhaust testing so that the PM filter is assured of only collecting airborne solid particles or liquid droplets. In the past, when relatively high concentrations of solid particles were present in engine exhaust, including both gasoline and diesel engines, collection of gas phase artifacts was not a significant issue. However, post 2007, heavy-duty highway diesel engines must meet a PM emissions level of 0.01 g/hp-hr, down from 0.1 g/hp./hr in 1998. Similarly, current EPA Tier 4 regulations for nonroad engines require an emission level of less than or equal to 0.02 g/hp-hr, down from 0.2 g/hp-hr. In addition, light duty engines must meet new regulations (EPA Tier 3) and CARB LEV III down from a current level of 10 mg/mile to 6 mg/mile in 2017 and 3 mg/mile by 2021, with a possible 1 mg/mile by 2025.

Figure 1:
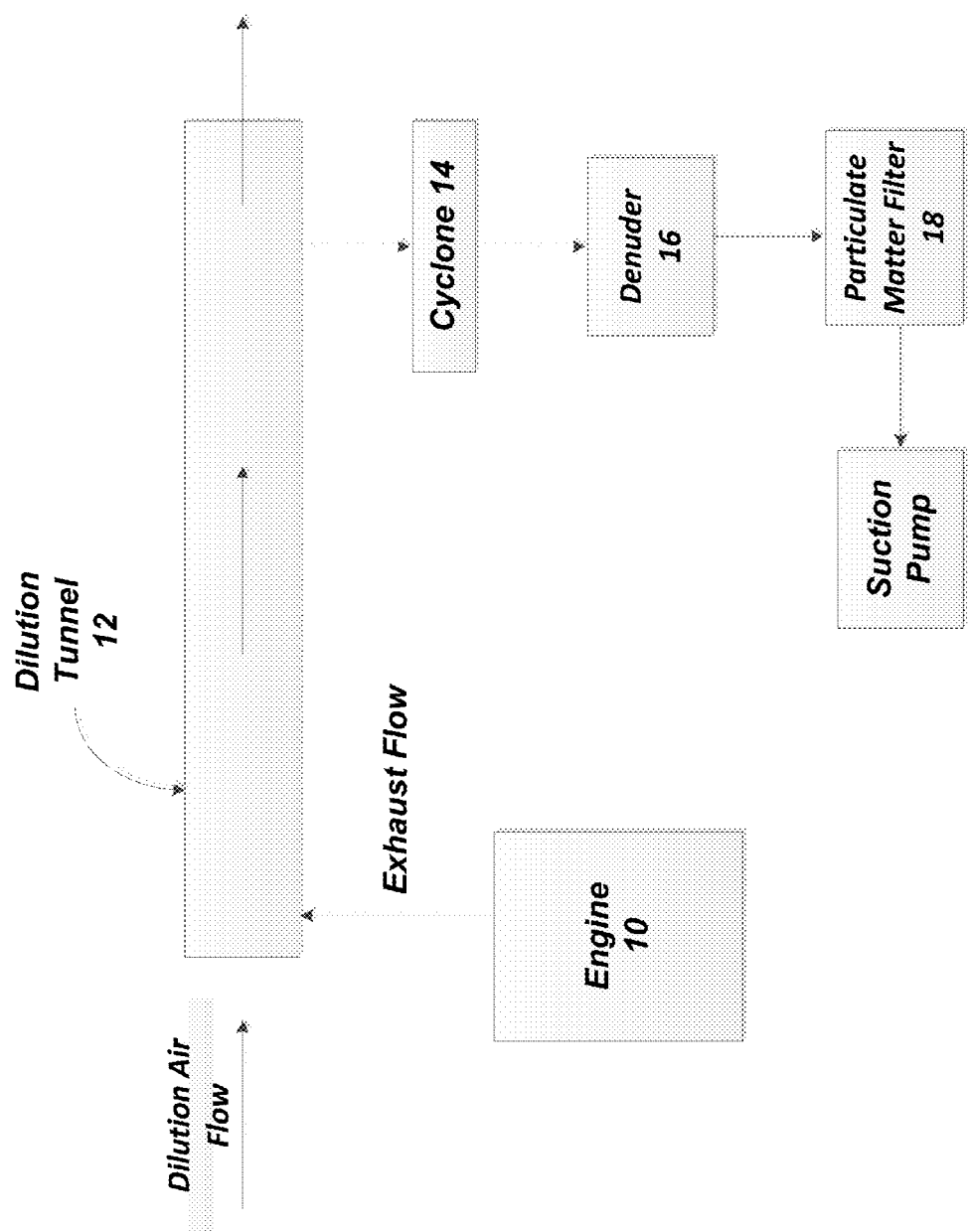
FIG. 1 illustrates the gas phase denuder and its position in a typical hydrocarbon combustion engine testing system.

Attention is directed to FIG. 1 which illustrates one preferred lay-out of the location of the gas phase denuder 16 of the present disclosure in the illustrated sampling system for engine 10 in general accordance with the Code of Federal Regulations CFR Part 1065 which employs a full flow dilution tunnel 12. The reference to a gas phase denuder herein is to be understood herein as a device to remove gas phase artifacts, prior to a particulate filter, and that would otherwise collect on the particulate filter, as described more fully herein.

As therefore illustrated, for any given hydrocarbon combustion engine 10, such as a diesel engine, during testing or sampling of the exhaust, the gas phase denuder 12 is positioned upstream of the particulate matter (PM) filter 18. Accordingly, regardless of the particular engine exhaust testing under consideration, the gas phase denuder herein is positioned upstream of the particulate matter filter 14 and operates to remove gas phase artifacts, which would otherwise interfere with the PM filter collection and accurate evaluation of a selected exhaust for regulatory compliance.

As shown, the exhaust flow form the engine 10 is first introduced into the dilution tunnel 12 where a dilution air flow is introduced. The dilution of air flow to exhaust gas may be in the range of 3:1 to 40:1 by volume. In addition, as illustrated, the gas phase denuder 16 is positioned downstream of the cyclone 14, which cyclone will filter and remove respiratory particles (i.e. particles greater than 2.5 µm). However, it should be appreciated that the denuder 16 may also be placed upstream of the cyclone 14. As noted above, the denuder herein can be used in any systems testing configuration provided it is used upstream of the particulate filter 18 such that more reliable particulate filter collection can be determined.

Figure 2:
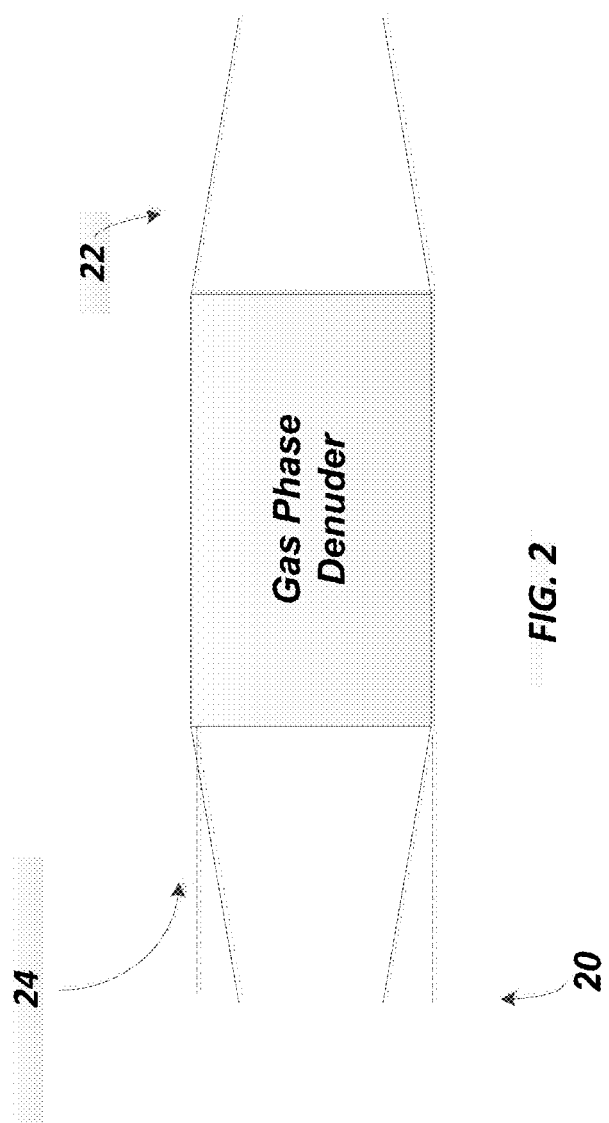
FIG. 2 illustrates the conical input and output port of the gas phase denuder.

In addition, to improve upon the performance of the gas phase denuder, it may preferably be fitted with a converging conical type inlet and converging conical outlet to avoid or minimize particle/aerosol losses at the inlet and outlet of the denuder and to facilitate coupling in the engine exhaust testing or sampling system. The opening for coupling may preferably be in the range of 0.25 inch to 1.0 inch. As illustrated in FIG. 2, a converging conical inlet 20 or outlet 22 may be employed which provides for relatively improved capture of solid particles or liquid droplets for passage to the particulate matter filter. Such converging inlet or outlet may preferably form an angle of 12.5° with respect to the horizontal plane as shown by arrow 24.

Gas phase artifacts are understood herein to include gaseous compounds of: (1) hydrocarbons having 4 or more carbon atoms; (2) sulfur dioxide and sulfate species such as $SO_2$, $SO_3$, $SO_4^{2-}$, $H_2SO_4$ and $(NH_4)_2SO_4$. Such gas phase compounds, if not removed, will tend to absorb onto the PM filter, thereby compromising the evaluation of particulate in a given exhaust stream undergoing evaluation (i.e. the gas phase compounds when absorbed on the PM filter would be improperly identified as particulate matter). It is worth noting that in the case of $H_2SO_4$ and/or $(NH_4)_2SO_4$, the gas phase denuder herein is such that if these compounds are present in the solid and/or liquid (particle) form, the gas phase denuder will allow for their passage. However, if present in gas form, the gas phase denuder will remove such gas phase compounds $H_2SO_4$ and $(NH_4)_2SO_4$ from the exhaust flow.

The gas phase denuder is also sized to discriminate between particle and/or aerosol phase (colloid of fine solid particles or liquid droplets) and the gas phase employing a gas and particle diffusion mechanism. Molecules such as hydrocarbons, sulfuric acid, and or $(NH_4)_2SO_4$ have a relatively higher diffusion coefficient than particles and aerosol. Thus, as these molecules enter the channels of the denuder, they generally migrate to the internal walls due to their high diffusion coefficient (much faster than particles) and are adsorbed onto the wall of the denuder. As a result, the gas phase molecules are lost onto the walls and the particle/aerosol phase materials are preserved and exit the denuder without interacting with the denuder internal walls.

The gas phase denuder herein is such that it is configured to operate (remove gas phase artifacts) at temperatures from −200° C. up to about 75° C. More preferably, the gas phase denuder is such that it will operate (remove gas phase artifacts) over the temperature range of 25° C. (+/−5° C.) to 47° C. (+/−5° C.). Accordingly, the gas phase denuder may preferably operate over the temperature range of 20° C. to 52° C.

The gas phase denuder also preferably operates within the engine environment at pressures from 0.1-2.0 atm, more preferably from 0.5-1.5 atm, and even more preferably from 0.7 atm to 1.3 atm. The gas phase denuder will also remove 90% or more by weight or volume of the gas phase artifacts. More specifically the denuder will remove 90% to 98% of the gas phase artifacts, which level was confirmed by measurement of the concentration of both hydrocarbons having 4 or more carbons, as well as sulfuric acid, upstream and downstream of the gas phase denuder 12.

The gas phase denuder is also characterized herein as one that provides 95% to 100% penetration (flow-through) of solid particles and/or liquid droplets in the size range of 5 nm to 1000 nm. That is, 95% to 100% of such solid particles and/or liquid droplets pass through the denuder to be collected on the particulate matter filter. More preferably, the gas phase denuder herein is one that provides 95% to 100% penetration of solid particles and/or liquid droplets in the size range of 20 nm to 500 nm. Such reference to the size of the solid particles or liquid droplets is reference to the largest cross-sectional dimension of either the particles or droplets, as appropriate.

The gas phase denuder herein is preferably formed from a substrate formed of ceramic material (non-metallic solid) and may therefore comprise a nitride, carbide, oxide, oxynitride, oxycarbide, or a combination of the foregoing. One may preferably utilize a cordierite substrate which is understood as a magnesium, iron, aluminum cyclosilicate with a formula of $(Mg, Fe)_2Al_3(Si_5AlO_{18})$. In addition, the substrate may be formed from metals such as iron, stainless steel, and/or any other metals that don't that have a melting point higher than 600° C. The substrate is preferably in the configuration of a cellular array such as a honeycomb array (typically square cells) wherein there are 100 cells/square inch to 800 cells per square inch. Preferably, the substrate has 300-500 cells/square inch, or more preferably 350 cells/square inch to 450 cells/square inch.

The denuder substrate preferably includes an Al-zeolite coating, which may be understood as an aluminosilicate material in which some of the silicon atoms have been replaced by aluminum. The chemical composition of the Al-zeolite may be expressed by the following formula: $M(2/n)O.Al_2O_3.ySiO_2.wH_2O$ where M represents a group 1A or IIA element, n is the cation valence, y is 2 or greater, and w is the number of water molecules contained in the channels or interconnected voids within the zeolite. The surface area provided by the denuder with the alumina-zeolite coating preferably falls in the range of 100 m²/gram to 200 m²/gram of the total mass of the cordierite substrate and the alumina-zeolite coating. For example, if the substrate is made of heavier materials than cordierite, the surface area per unit mass will be lower than the one reported above, but the total surface area of the denuder can range from 5,000 m² to 15,000 m² and does not change. The alumina-zeolite coating can range from 150 to 300 gram/liter of substrate sample, with an equal mass between alumina and zeolite or other mass weighting. In addition, the gas phase denuder herein is further characterized as having a space velocity range from 6000/hour to 20,000/hour. Space velocity (SV)=(denuder volume flow/hour)/denuder volume.

The gas phase denuder herein is also one that is capable of regeneration once it has maximized its ability to remove gas phase artifacts. More specifically, the gas phase denuder is such that it may be regenerated under conditions of elevated temperature exposure, such as exposure to temperatures up to 600° C. for a period of 12 hours. This may be achieved by heat wrapping of the denuder or placement of the denuder in an appropriate oven. One may also reduce pressure during regeneration (i.e. apply a vacuum down to 0.001 atm, in which case it has been observed that regeneration, and purging of the absorbed gas artifacts, is more readily achieved. One may also monitor the purging of the absorbed gas artifacts during regeneration to determine the optimal time for regeneration. Such monitoring includes detection of one or more of the absorbed gases noted herein.

The gas phase denuder here has also been found to be suitable for applications as applied to a condensation particle counters (CPC). A condensation particle counter typically includes a saturator, a condenser and an optical particle counter (OPC) and is widely used in measuring the number and size of fine particles. The saturator of the condensation particle counter contains working fluid to saturate an aerosol, i.e., a particle-suspended gas. Examples of the working fluid include alcohol-based fluids such as butanol or isopropyl alcohol or ethylene glycol. The CPC detects and counts particles by enlarging them by using the particles as nucleation centers to create droplets in a supersaturated gas of the alcohol-based fluids. After detection, the particles are collected on a filter, but the exhaust stream of the CPC still contains residual alcohol.

Figure 3:
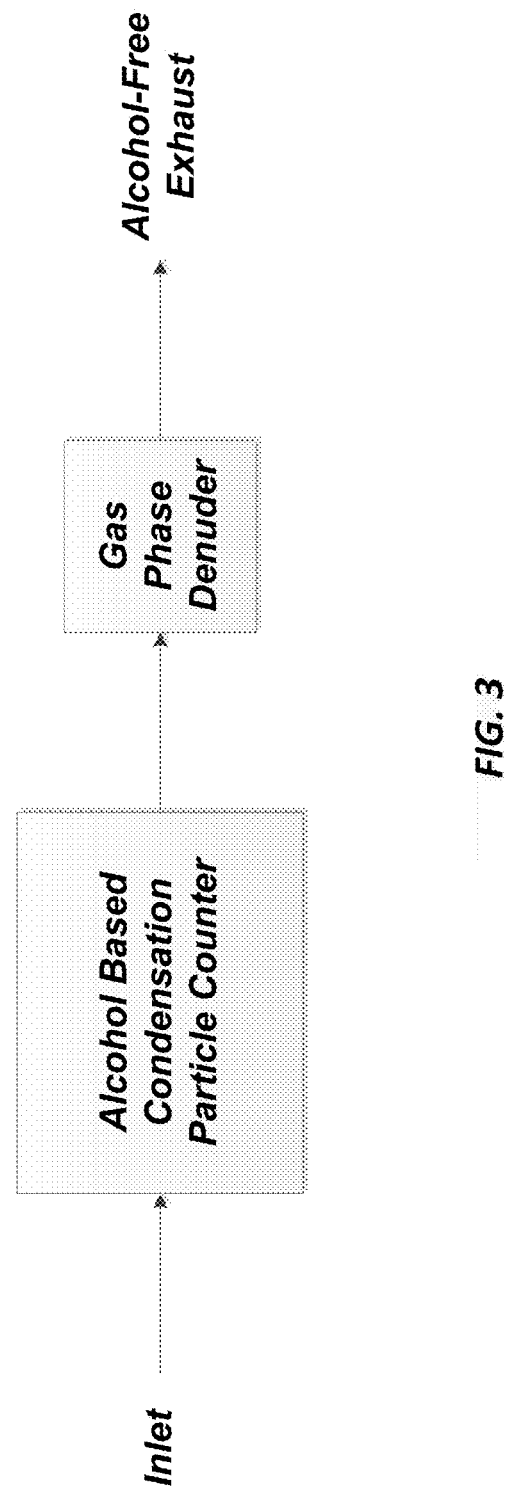
FIG. 3 illustrates the gas phase denuder as applied to the removal of alcohols from the output of an alcohol based condensation particle counter.

As illustrated in FIG. 3, the gas phase denuder herein may be conveniently positioned at the output end of a CPC. As illustrated, the gas phase denuder will operate to capture and reduce the alcohol that may be otherwise present in the CPC exhaust. Similar to the above, the denuder preferably includes an aluminum-zeolite coating on an underlying substrate, preferably made of cordierite, and operates at a temperature range of 25° C. to 47° C. and at pressures from 0.1-2.0 atm, more preferably from 0.5-1.5 atm, and even more preferably from 0.7 atm to 1.3 atm. The denuder was then observed to remove 90% to 98% by weight or volume of the alcohol in the CPC exhaust, wherein such alcohol, as noted, is typically butanol.

What is claimed is:

1. A method for removal of gas phase artifacts from an exhaust stream of a hydrocarbon combustion engine undergoing evaluation for the presence of particulate matter as collected on a particulate matter filter comprising:
    diluting said exhaust stream with a dilution air flow to provide a diluted exhaust stream that includes solid particles or liquid droplets in the size range of 5 nm to 1000 nm;
    passing said diluted exhaust stream through a cyclonic separator to remove respiratory particles from said diluted exhaust stream;
    passing said diluted exhaust stream through a gas phase denuder that includes a cellular cordierite substrate having an aluminum-zeolite coating, wherein said gas phase denuder exhibits a surface area in the range of 5,000 m² to 15,000 m²;
        wherein said gas phase denuder removes 90% by weight or volume said gas phase artifacts from said diluted exhaust stream, said gas phase artifacts including one or more of the following:
            (a) hydrocarbons having four or more carbon atoms; or
            (b) sulfur dioxide and sulfate species of the formulas $SO_2$, $SO_3$, $SO_4^{2-}$, $H_2SO_4$ and $(NH_4)_2SO_4$ and;
        wherein said gas phase denuder passes 95% to 100% of said solid particles or liquid droplets in said diluted exhaust stream for collection by a downstream particulate filter.

2. The method of claim 1 wherein said gas phase denuder cellular substrate includes 100 cells/square inch to 800 cells/square inch.

3. The method of claim 1 wherein said gas phase denuder has a space velocity of 6000/hour to 20,000/hour.

4. The method of claim 1 wherein said solid particles or liquid droplets comprise particles or droplets at a size range of 20 nm to 500 nm.

5. The method of claim 1 wherein said gas phase denuder is maintained at a temperature of −200° C. to 52° C.

6. The method of claim 5 wherein said gas phase denuder is maintained at a temperature of 20° C. to 52° C.

7. The method of claim 1 wherein said gas phase denuder is maintained at a pressure of 0.1 atm to 2.0 atm.

8. A method for removal of gas phase artifacts from an exhaust stream of a hydrocarbon combustion engine undergoing evaluation for the presence of particulate matter as collected on a particulate filter comprising:
    positioning a dilution tunnel to receive the exhaust stream of the hydrocarbon combustion engine undergoing evaluation and a dilution air flow;
    positioning a cyclonic separator to receive the diluted exhaust stream from the dilution tunnel to remove respiratory particles from said diluted exhaust stream;
    positioning a gas phase denuder in said diluted exhaust stream at a location upstream of said particulate filter, wherein said diluted exhaust stream includes solid particles or liquid droplets in the size range of 5 nm to 1000 nm, and wherein said gas phase denuder comprises a cellular cordierite substrate with 100 cells/square inch to 800 cells/square inch, said cells having an aluminum-zeolite coating, and wherein said gas phase denuder exhibits a surface area in the range of 5,000 m² to 15,000 m²;
    feeding said diluted exhaust stream through said gas phase denuder wherein said gas phase denuder is maintained at a temperature of 20° C. to 52° C. and removing 90% by weight or volume of said gas phase artifacts in said diluted exhaust stream wherein said gas phase artifacts comprise one or more of:
    (a) hydrocarbons having four or more carbon atoms; or
    (b) sulfur dioxide and sulfate species of the formulas $SO_2$, $SO_3$, $SO_4^2$, $H_2SO_4$ and $(NH_4)_2SO_4$;
    wherein said gas phase denuder passes 95% to 100% of said solid particles or liquid droplets in said diluted exhaust stream to pass through said denuder for collection on said particulate filter.

9. A filtration apparatus for hydrocarbon combustion engine exhaust stream containing gas phase artifacts and solid or liquid droplets, the exhaust stream undergoing evaluation for the presence of particulate matter as collected on a particulate matter filter, the apparatus comprising:
 a dilution tunnel to receive the hydrocarbon combustion engine exhaust stream and a dilution air flow to provide a diluted exhaust stream;
 a cyclonic separator to remove respiratory particles from said diluted exhaust stream;
 a particulate matter filter for collecting said solid or liquid droplets; and
 a gas phase denuder in said exhaust stream at a location upstream of said particulate filter,
  wherein said exhaust includes solid particles or liquid droplets in the size range of 5 nm to 1000 nm;
  wherein said gas phase denuder comprises a cellular cordierite substrate having an aluminum-zeolite coating that absorbs 90% by weight or volume of one or more of:
   (a) hydrocarbons having four or more carbon atoms; or
   (b) sulfur dioxide and sulfate species of the formulas $SO_2$, $SO_3$, $SO_4^{2-}$, $H_2SO_4$ and $(NH_4)_2SO_4$; and
  wherein said gas phase denuder provides for 95% to 100% passage of said solid particles or liquid droplets in said diluted exhaust stream for collection on said particulate matter filter, and wherein said gas phase denuder exhibits a surface area in the range of 5,000 $m^2$ to 15,000 $m^2$.

10. The apparatus of claim 9 wherein said gas phase denuder is configured to operate at a temperature of 20° C. to 52° C.

11. The apparatus of claim 9 wherein said gas phase denuder is configured to operate at a pressure of 0.1 atm to 2.0 atm.

12. The method of claim 1 wherein diluting said exhaust stream with said dilution air flow to provide a diluted exhaust stream comprises:
 diluting said exhaust stream with a dilution air at a dilution air to exhaust stream ratio of from about 3:1 to about 40:1 by volume.

13. The method of claim 1 wherein passing said diluted exhaust stream through a cyclonic separator to remove respiratory particles from said diluted exhaust stream comprises:
 passing said diluted exhaust stream through a cyclonic separator positioned upstream of the gas phase denuder to remove respiratory particles from said diluted exhaust stream.

14. The method of claim 1 wherein passing said diluted exhaust stream through a cyclonic separator to remove respiratory particles from said diluted exhaust stream comprises:
 passing said diluted exhaust stream through a cyclonic separator positioned downstream of the gas phase denuder and upstream of the particulate matter filter to remove respiratory particles from said diluted exhaust stream.

* * * * *